United States Patent

Clark et al.

Patent Number: 6,054,448
Date of Patent: Apr. 25, 2000

[54] 2-AMINO-2-(3-SUBSTITUTED CYCLOBUTYL) ACETIC ACID DERIVATIVES

[75] Inventors: Barry Peter Clark, Lower Froyle; John Richard Harris, Guildford, both of United Kingdom

[73] Assignee: Eli Lilly and Company Limited, Basingstoke, United Kingdom

[21] Appl. No.: 08/954,675

[22] Filed: Oct. 17, 1997

[30] Foreign Application Priority Data

Oct. 18, 1996 [GB] United Kingdom ............. 9621789

[51] Int. Cl.[7] ................ A61K 31/195; A61K 31/66; C07C 61/04

[52] U.S. Cl. ................ 514/183; 514/96; 514/100; 514/75; 514/140; 514/217; 514/212; 514/298; 514/381; 514/431; 514/437; 514/450; 514/454; 514/572; 540/522; 546/108; 549/26; 549/354; 549/388

[58] Field of Search .................. 514/75, 96, 100, 514/140, 212, 298, 431, 437, 450, 454, 572; 540/522; 546/108; 549/26, 354, 388; 558/52, 60; 562/24, 499, 505

[56] References Cited

U.S. PATENT DOCUMENTS 5,717,109  2/1998  Arnold et al. ............. 548/511

FOREIGN PATENT DOCUMENTS

| WO 93/21176 | 10/1993 | WIPO . |
| WO 95/15940 | 6/1995 | WIPO . |
| WO 96/07405 | 3/1996 | WIPO . |

OTHER PUBLICATIONS

Brodi et al., Progress in Neurobiology; vol. 59 pp. 55–79, 1999.

*Primary Examiner*—John M. Ford
*Assistant Examiner*—Pavanaram K Sripada
*Attorney, Agent, or Firm*—Martin A. Hay

[57] ABSTRACT

Compounds of the formula

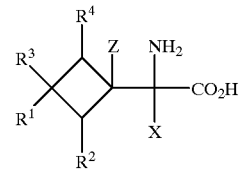

(I)

in which $R^1$ is
Y or Y—$C_{1-6}$ alkyl, where Y is carboxy, tetrazolyl, —$SO_2H$, —$SO_3H$, —$OSO_3H$, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or optionally substituted phenyl-$C_{1-6}$ alkyl,
and $R^2$, $R^3$, $R^4$, X and Z are as defined in the specification, possess affinity for metabotropic glutamate receptors and are useful in the treatment of disorders of the central nervous system.

10 Claims, No Drawings

2-AMINO-2-(3-SUBSTITUTED CYCLOBUTYL) ACETIC ACID DERIVATIVES

This invention relates to novel compounds and their use as pharmaceuticals.

It is well known that excitatory neurotransmission in the mammalian central nervous system is primarily mediated by the amino acid, L-glutamate, acting on ionotropic and metabotropic receptors, and compounds that modify neurotransmission by interaction with these receptors are of interest for their potential use in the treatment of disorders of the central nervous system.

The compounds of the invention are of the formula:

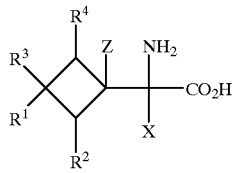

in which $R^1$ is

Y or Y—$C_{1-6}$ alkyl, where Y is carboxy, tetrazolyl, —$SO_2H$, —$SO_3H$, —$OSO_3H$, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or optionally substituted phenyl-$C_{1-6}$ alkyl, $R^2$, $R^3$ and $R^4$ are each hydrogen, hydroxyl, halo, carboxy, $C_{1-6}$ alkyl, carboxy-$C_{1-6}$ alkyl, optionally substituted phenyl, optionally substituted phenyl-$C_{1-6}$ alkyl or $C_{2-6}$ alkenyl, X and Z are each hydrogen, $C_{1-6}$ alkyl, $C_{3-7}$ cycloalkyl, optionally substituted phenyl, optionally substituted phenyl-$C_{1-6}$ alkyl, optionally substituted naphthylmethyl, optionally substituted anthracenylmethyl,

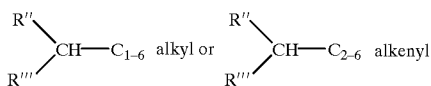

where R" and R'" are optionally substituted phenyl, or

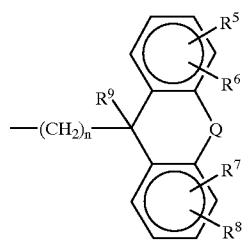

where n is 0 or 1 to 3, Q is —O—, —NR""—, —S—, —SO—, —$SO_2$—, —$CH_2$—, —CH=CH—, —$CH_2S$—, —$CH_2O$—, —$CH_2CH_2$— or —CONR"" where R"" is hydrogen or $C_{1-6}$ alkyl, and $R^5$, $R^6$, $R^7$, $R^8$ and $R^9$ are each hydrogen, halo, $C_{16}$ alkyl, $C_{1-6}$ alkyloxy or hydroxy;

provided that one of X and Z is hydrogen, or both of X and Z are hydrogen;

or a salt or ester thereof.

A particular group of compounds according to the invention is of formula (I) above in which $R^1$ is Y or Y—$C_{1-6}$ alkyl, where Y is carboxy, tetrazolyl, —$SO_2H$, —$SO_3H$, —$OSO_3H$, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or optionally substituted phenyl-$C_{1-6}$ alkyl, $R^2$, $R^3$ and $R^4$ are each hydrogen, hydroxyl, halo, carboxy, $C_{1-6}$ alkyl, carboxy-$C_{1-6}$ alkyl, optionally substituted phenyl, optionally substituted phenyl-$C_{1-6}$ alkyl or $C_{2-6}$ alkenyl, X and Z are hydrogen, $C_{1-6}$ alkyl, $C_{3-7}$ cycloalkyl, optionally substituted phenyl, optionally substituted phenyl-$C_{1-6}$ alkyl,

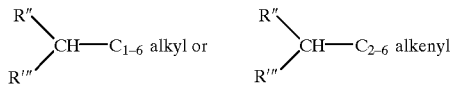

where R" and R'" are optionally substituted phenyl, or

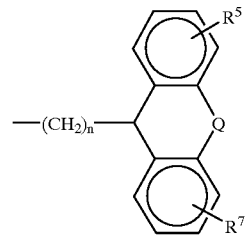

where n is 0 or 1 to 3, Q is —O—, —NH—, —S—,— CONH— or —$CH_2CH_2$—, and $R^5$ and $R^7$ are each hydrogen, halo or $C_{1-6}$ alkyl;

provided that one of X and Z is hydrogen, or both of X and Z are hydrogen;

or a salt or ester thereof.

A further group of compounds of the invention is of formula (I) above in which $R^1$ is Y or Y—$C_{1-6}$ alkyl-, where Y is carboxy, tetrazolyl, —$SO_2H$, —$SO_3H$, —$OSO_3H$ or —CONHOH, $R^2$, $R^3$ and $R^4$ are each hydrogen, hydroxyl, halo, carboxy, $C_{1-6}$ alkyl, carboxy-$C_{1-6}$ alkyl, optionally substituted phenyl, optionally substituted phenyl-$C_{1-6}$ alkyl or $C_{2-6}$ alkenyl, X and Z are each hydrogen, $C_{1-6}$ alkyl, $C_{3-7}$ cycloalkyl, optionally substituted phenyl, optionally substituted phenyl-$C_{1-6}$ alkyl, optionally substituted naphthylmethyl, optionally substituted anthracenylmethyl,

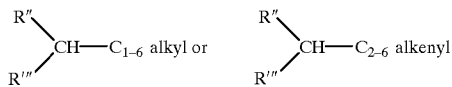

where R" and R'" are optionally substituted phenyl, or

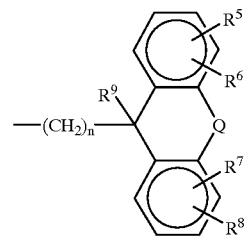

where n is 0 or 1 to 3, Q is —O—, —NR""—, —S—, —SO—, —$SO_2$—, —$CH_2$—, —CH=CH—, —$CH_2S$—, —CH$_2$O—, —CH$_2$CH$_2$— or —CONRl'''' where R'''' is hydrogen or C$_{1-6}$ alkyl, and R$^5$, R$^6$, R$^7$, R$^8$ and R$^9$ are each hydrogen, halo, C$_{1-6}$ alkyl, C$_{1-6}$ alkyloxy or hydroxy;

provided that one of X and Z is hydrogen, or both of X and Z are hydrogen;

or a salt or ester thereof.

The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above general formula, a C$_{1-6}$ alkyl group can be straight or branched chain, such as, for example, methyl, ethyl, propyl, isopropyl, butyl and isobutyl, and is preferably methyl or ethyl. A Y—C$_{1-6}$ alkyl, or carboxy-C$_{1-6}$ alkyl group is one such alkyl group substituted by Y— or carboxy as, for example, Y(CH$_2$)$_m$— or HO$_2$C(CH$_2$)$_m$ where m is 1 to 6. A C$_{2-6}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula R—CH=CH— where R is C$_{1-4}$ alkyl. An optionally substituted phenyl-C$_{2-6}$ alkenyl is an optionally substituted phenyl linked through one such alkenyl group. A C$_{3-7}$ cycloalkyl group is preferably, for example, cyclopropyl, cyclopentyl or cyclohexyl and these groups may optionally be substituted by one or two methyl substituents.

A halo substituent group can be fluoro, chloro, bromo or iodo, and is preferably chloro.

In the above Formula (I), an optionally substituted phenyl is optionally substituted with, for example, one or more substituents, preferably 1 to 3 substituents, selected from C$_{1-4}$ alkyl, especially methyl, C$_{1-4}$ alkoxy, especially methoxy and ethoxy, carboxy, hydroxy, cyano, halo, especially bromo, chloro and fluoro, trifluoromethyl, nitro, amino, C$_{1-4}$ acylamino and C$_{1-4}$ alkylthio. When substituted, a phenyl group is preferably substituted by one to three substituents. An optionally substituted phenyl-C$_{1-6}$ alkyl group is one such group linked through an alkylene chain, for example, phenyl-(CH$_2$)$_p$ where p is 1 to 6, and a most preferred example is benzyl. An optionally substituted naphthylmethyl or optionally substituted anthracenylmethyl can be substituted on one or more phenyl rings as described above for optionally substituted phenyl.

In the above formula (I), Y is preferably carboxy, tetrazolyl, —SO$_2$H, —SO$_3$H, —OSO$_3$H or —CONHOH, and is especially carboxy. Preferred values of R$^1$ are carboxy, tetrazolyl, —SO$_2$H, —SO$_3$H, —OSO$_3$H, —CONHOH and carboxy-C$_{1-6}$ alkyl, and especially preferred values are carboxy and carboxy-C$_{1-6}$ alkyl, carboxy being most preferred of all.

When X or Z is a diphenyl moiety it is preferably of the formula

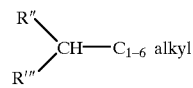

and is more preferably an optionally substituted diphenylethyl group, especially diphenylethyl itself. When X or Z is:

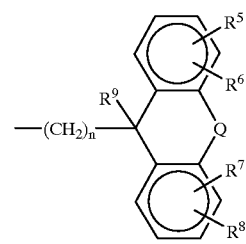

n is preferably 1, and Q —O— or —S—. The group R$^9$ is preferably hydrogen. The phenyl substituents R$^5$, R$^6$, R$^7$ and R$^8$ are preferably hydrogen or halo, and R$^6$ and R$^8$ most preferably hydrogen. Preferred examples are xanthylmethyl and thioxanthylmethyl.

A preferred group of compounds is one in which R$^2$, R$^3$ and R$^4$ are each hydrogen, hydroxyl, halo, carboxy, C$_{1-6}$ alkyl, carboxy-C$_{1-6}$ alkyl, optionally substituted phenyl or optionally substituted phenyl C$_{1-6}$ alkyl.

The substituents R$^2$ and R$^4$ are more preferably hydrogen, carboxy or optionally substituted phenyl, and most preferably hydrogen. The group R$^3$ is preferably hydrogen or carboxy, and especially hydrogen.

It is further preferred that Z is hydrogen.

A preferred group of compounds is one of formula (I) above, in which R$^1$ is —CO$_2$H, R$^2$, R$^3$ and R$^4$ are all hydrogen, and X is R''R'''CH—C$_{1-6}$ alkyl or

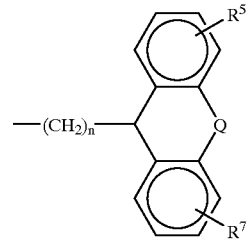

where n is 1 and Q is —O—; and salts and esters thereof. A further preferred group is one such compound in which Q is —S—. Such compounds are preferably of S-configuration at the amino acid a-carbon.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention can exhibit geometric isomerism and can contain one or more asymmetric carbon atoms, and this gives rise to enantiomers and diasteriomers. The compounds can be prepared as racemates or as enantiomers, and individual enantiomers can be isolated from racemates by conventional techniques such as, for example, resolution by crystallisation of the salt with L-lysine, if so desired.

The invention also includes a process for producing a compound of the invention, which comprises hydrolysing:

1) a compound of the formula:

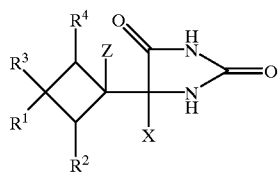

(II)

2) a compound of the formula:

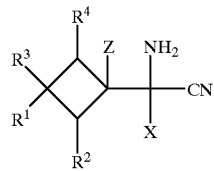

(III)

or 3) a compound of the formula:

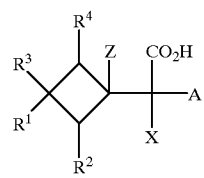

(IV)

where R is an ester group, preferably $C_{1-4}$ alkyl, and A is —NHCHO or —N=C=O.

With regard to process variant (1), this reaction is preferably carried out in a solvent such as, for example, water, at an elevated temperature of from 50° C. to 200° C., and in the presence of an acid or base such as, for example, hydrochloric acid or sodium hydroxide. The intermediate compound of formula (II) can be prepared by reacting a compound of formula:

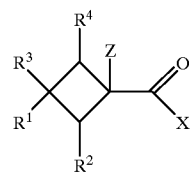

(V)

with potassium cyanide and ammonium carbonate in aqueous ethanol under the conditions of the Bucherer Bergs reaction, at a temperature of, for example, 30° C. to 120° C.

Compounds of formula (V) can be synthesised by a number of routes. For example, reaction of the carboxylic acid:

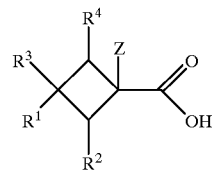

suitably protected when one or more of $R^1$ to $R^4$ is carboxy, with oxalyl chloride gives the acid chloride which, when reacted with organozinc reagents X—ZnI by means of a Knochel coupling, yields the compound (V). Alternatively, when X is the group:

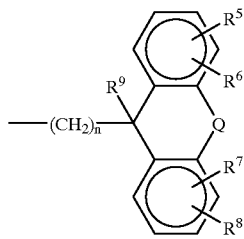

and $R^9$ is hydrogen or $C_{1-6}$ alkyl, a compound of formula (V) can be prepared from the acid chloride, referred to above, by reaction with a malonate reagent of formula $LiO_2CCHLiCO_2Et$ to give a keto ester which on reaction with acetic acid and

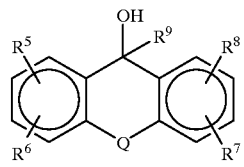

gives an intermediate that when hydrolysed and decarboxylated provides the compound of formula (V):

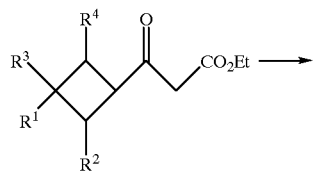

-continued

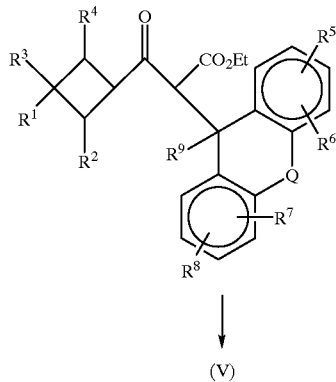

(V)

With regard to process variant (2), this reaction is preferably carried out in a solvent such as, for example, water, at an elevated temperature of from 30° C. to 200° C., and in the presence of an acid or base such as, for example, hydrochloric acid. The intermediate compound (III) can be prepared by reacting a compound of formula (V) with potassium cyanide and ammonium chloride according to the Strecker reaction.

With regard to process variant (3), this reaction is preferably carried out in a solvent such as, for example, tetrahydrofuran and water, at an elevated temperature of from 50° C. to 150° C., and in the presence of an acid or base such as, for example, sodium hydroxide. The intermediate of formula (IV) can be prepared from a ketone of the formula:

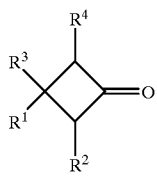

by reaction with $NC.CH_2CO_2Me$ to give a dehydroamino acid, which on reduction with, for example, hydrogen and palladium, or sodium borohydride, provides the formamide compound of formula (IV). When Z in formula (I) is other than hydrogen, the intermediate compound can be prepared by reacting the dehydromalonate with an organo-copper reagent, which results in conjugate addition of the Z group. The isocyanate compound of formula (IV) can be prepared by dibenzylation of a compound of formula:

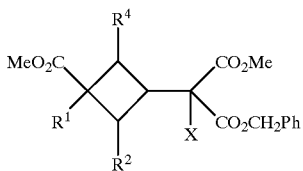

formation of the azide and rearrangement by the Curtius method.

The compounds of formula (II) above, and salts and esters thereof, are novel, and are included as a further aspect of the invention.

The compounds of the invention can also be prepared, by known methods, from intermediates of the type:

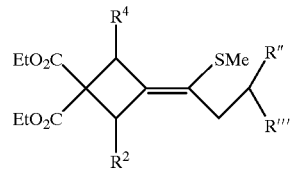

The compounds of the invention have pharmaceutical activity. They have been shown to possess affinity for metabotropic glutamate receptors.

Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-aspartate, AMPA, and kainate (Sommer B. and Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. and Conn J. P., Trends Pharmacol. Sci. 14: 13–20, 1993). Metabotropic glutamate receptors can be selectively activated by 1S,3R-1-aminocyclopentane-1,3-dicarboxylic acid (1S,3R-ACPD).

The compounds of the invention block the metabotropic glutamate receptor second messenger responses with IC50 values of less than 100 $\mu$M, including stimulation of phosphoinositide hydrolysis by agonist (see Schoepp D. D., Johnson B. G., True R. A., and Monn J. A., Eur. J. Pharmacol.—Mol. Pharmacol. Section 207: 351–353, 1991, and Kingston A. E. et al., Neuropharmacology 34, N8, 887–894, 1995).

Some of the compounds also reverse 1S,3R-ACPD-induced inhibition of forskolin-stimulated cAMP formation (Schoepp D. D., Johnson B. G., and Monn J. A., J. Neurochem. 58: 1184–1186, 1992). Affinity of some of the compounds for metabotropic glutamate receptors has also been demonstrated by the selective displacement of 1S,3R-ACPD-sensitive $^3$H-glutamate binding to rat brain cell membranes, a test for metabotropic glutamate receptor activity (Schoepp D. D. and True R. A., Neuroscience Lett. 145: 100–104, 1992).

The compounds of the invention are thus indicated for use in the treatment of neurological disorders such as acute neurodegenerative diseases, for example stroke, cerebral ischemia and head and spinal cord trauma, and chronic neurodegenerative diseases such as for example Alzheimer's disease, Parkinson's disease, Amyotrophic lateral sclerosis, AIDS-induced dementia and Huntington's Chorea. The compounds are also indicated for use as antipsychotic, anticonvulsant, analgesic and anti-emetic agents. They are also of potential use as anxiolytic and antidepressant agents.

The invention also includes a pharmaceutical composition comprising a pharmaceutically-acceptable diluent or carrier in association with a compound of Formula (I), or a pharmaceutically-acceptable salt thereof.

The compounds may be administered by various routes, for example, by the oral or rectal route, topically or parentally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

2-Amino-2-(3-cis-carboxycyclobutyl)-3-(9-xanthyl) propionic acid and 2-amino-2-(3-trans-carboxycyclobutyl)-3-(9-xanthyl)propionic acid i) Cis- and trans-3-phenylcyclobutanecarboxylic acid A stirred mixture of solid 3-phenylcyclobutane-1,1-dicarboxylic acid (44 g, 0.2 mol) was heated to 210° C. for 30 minutes. The solid melted and carbon dioxide effervesced to give the title prouct as a pale yellow liquid (a 1:1 mixture of cis- and trans-isomers).

ii) Phenacyl cis- and trans-3-phenylcyclobutane carboxylate

To a stirred solution of cis- and trans-3-phenylcyclobutanecarboxylic acid (26.5 g, 0.15 mol) in dried dimethylformamide (50 ml) was added phenacyl bromide (30 g, 0.15 mol), followed by solid potassium fluoride (19.1 g, 0.33 mol). After 2 hours at room temperature, the suspension was poured onto water (250 ml) and extracted with diethyl ether (2×150 ml). The extracts were washed with 0.1M aqueous potassium carbonate (3×100 ml), brine solution (200 ml), dried over anhydrous sodium sulphate, filtered and evaporated to give the title product as a yellow oil.

iii) Phenacyl cis- and trans-3-(carboxy)cyclobutane carboxylate

Ruthenium trichloride hydrate (750 mg) was added to a mechanically stirred mixture of phenacyl cis- and trans-3-phenyl-cyclobutanecarboxylate (44 g, 150 mmol), periodic acid (486 g, 2.13 mol), water (450 ml), acetonitrile (300 ml) and carbon tetrachloride (300 ml) at room temperature. The dark reaction mixture was stirred vigorously to mix the two layers and the mildly exothermic reaction was maintained at 25–35° C. by external cooling.

After 16 hours, the mixture was cooled and diethyl ether (600 ml) added with vigorous stirring. The ether layer was separated, washed with brine solution (4×200 ml), dried, filtered and evaporated to a brown oil. The crude product was purified by chromatography on flash silica, eluting with diethyl ether:petroleum ether 40–60 2:1, to give the title product as a waxy solid.

iv) Phenacyl cis- and trans-3-[(9-xanthyl)methylketo] cyclobutanecarboxylate

Phenacyl cis- and trans-3-(carboxy)cyclobutane carboxylate (1.15 g, 4.4 mmol) was dissolved in oxalyl chloride (3 ml) at room temperature. The solution slowly effervesced and after 1 hour was evaporated. The residual oil was redissolved in dried toluene (10 ml), evaporated again and redissolved in toluene to give a solution of the acid chloride.

A mixture of (9-xanthyl)methyl iodide (1.70 g, 5.3 mmol) and zinc/copper couple (0.82 g, 12.7 mmol) in dried toluene (17 ml) and dimethyl acetamide (2.4 ml) was stirred at 60° C. for 3 hours under nitrogen atmosphere. Tetrakis (triphenylphosphine)palladium[O] (0.24 g, 0.21 mmol) was added and after 5 minutes at 60° C. allowed to cool to room temperature. A solution of the above acid chloride was added and the mixture stirred for 1 hour at room temperature. The reaction mixture was diluted with ethyl acetate (30 ml), water (1 ml) and filtered through a pad of celite. The filtrate was washed with brine solution (2×20 ml), dried, filtered and evaporated to a yellow oil (3.18 g). The crude product was purified by chromatography on flash silica, eluting with 2% methanol in chloroform, to give the title product as a yellow oil.

v) Cis- and trans-3-[(9-xanthyl)methylketo] cyclobutanecarboxylic acid

Method 1

A mixture of phenacyl cis- and trans-3-[(9-xanthyl) methylketo]cyclobutane carboxylate (0.34 g, 0.77 mmol) and 2M sodium hydroxide (1 ml, 2 mmol) in ethanol (3.5 ml) was stirred at room temperature for 20 hours. Water (3 ml) was added and the mixture acidified with 2M hydrochloric acid (1.1 ml) to precipitate an oil. The mixture was extracted with dichloromethane (2×5 ml) and the extracts dried, filtered and evaporated to a yellow oil containing product and phenacyl alcohol. The oil was treated with water (5 ml) and 2M sodium hydroxide (1 ml) and the aqueous washed with diethyl ether (3×5 ml). The aqueous solution was acidified with 2M hydrochloric acid (1.2 ml) and extracted with dichloromethane (2×5 ml). The extracts were dried, filtered and evaporated to give the title product as a waxy solid.

Method 2

A stirred solution of ethyl 2-(9-xanthyl)-3-oxo-3-[3-(phenacylmethyloxycarbonyl)cyclobutyl]propanate (3.0 g, 5.8 mmol), aqueous 2M sodium hydroxide (14.5 ml, 29 mmol) and ethanol (14.5 ml) was heated under reflux for 20 hours. The mixture was evaporated to a small volume and then redissolved in water (30 ml). The basic aqueous solution was washed with diethyl ether (2×30 ml) and then acidified to pH1 with 5M hydrochloric acid (10 ml). The acidic aqueous was extracted with diethyl ether (2×30 ml) and the extracts were then dried, filtered and evaporated to give a yellow oil (2.04 g). Chromatography on flash silica, eluting with diethyl ether, gave the title product as a waxy solid.

vi) Ethyl 3-oxo-3-[3-(phenacylmethyloxy carbonyl) cyclobutyl]propanate

Phenacyl cis- and trans-3-(carboxy)cyclobutane carboxylate (7.86 g, 30 mmol) was dissolved in oxalyl chloride (18 ml) at room temperature. The solution effervesced and after 30 minutes was evaporated. The residual oil was redissolved in dried toluene (20 ml), evaporated again and redissolved in dried tetrahydrofuran (40 ml) to give a solution of the acid chloride.

A solution of n-butyl lithium (2.5M) in n-hexane (40.8 ml, 102 mmol) was added dropwise over 10 minutes to a vigorously stirred solution of monoethyl malonate (6.73 g, 51 mmol) in dried tetrahydrofuran (100 ml), and cooled to −60° C. under nitrogen atmosphere. The temperature was allowed to rise to −5° C. during the addition. After 10 minutes at −5° C., the mixture was recooled to 60° C. and a solution of the acid chloride added dropwise over 5 minutes to the suspension. After 30 minutes at −60° C., the mixture was allowed to warm to −30° C. and then poured onto vigorously stirred diethyl ether (200 ml) and aqueous hydrochloric acid (1M, 120 ml). The ether layer was separated, washed with water (200 ml), saturated aqueous sodium bicarbonate (3×200 ml), brine (2×100 ml) and then dried, filtered and evaporated to give a brown oil. The product was purified by chromatography on flash silica eluting with chloroform containing 1% methanol and increasing to 2.5% methanol, to give the title product as a yellow oil.

vii) Ethyl 2-(9-xanthyl)-3-oxo-3-[3-(phenacylmethyloxycarbonyl)cyclobutyl]propanate Acetic acid (20 ml) was added to a stirred suspension of 9-hydroxyxanthene (3.96 g, 20 mmol) and ethyl 3-oxo-3-[3-(phenacylmethyloxycarbonyl) cyclobutyl]propanate (6.0 g, 18 mmol) in ethanol (20 ml) at room temperature. A clear solution formed and was allowed to stand for 7 days at room temperature.

The reaction mixture was diluted with water (100 ml) and extracted with diethyl ether (2×100 ml). The ether extracts were washed with saturated aqueous sodium bicarbonate (3×100 ml), brine solution (100 ml) and then dried, filtered and evaporated to a yellow oil. Purification by chromatography on flash silica (eluting with chloroform containing 1% methanol increasing to 2% methanol) gave the title product as a yellow oil.

viii) 5-(Cis- and trans-3-carboxycyclobutyl)-5-[(9-xanthyl) methyl]imidazolidine-2,4-dione A stirred mixture of cis- and trans-3-[(9-xanthyl) methylketo]cyclobutanecarboxylic acid (1.70 g, 5.3 mmol), potassium cyanide (0.69 g, 10.6 mmol) and ammonium carbonate (2.0 g, 21.2 mmol) in ethanol-water (1:1, 10 ml) was heated to 80° C. for 16 hours in a PTFE lined stainless steel pressure vessel. The cold mixture was diluted with water (30 ml) and cautiously acidified by dropwise addition of 5M hydrochloric acid (10 ml). The stirred mixture effervesced and a thick solid precipitated. The solid was filtered, washed with 0.1M hydrochloric acid (2×10 ml) and dried in vacuo to give the title product as a white solid.

ix) 2-Amino-2-(3-cis-carboxycyclobutyl)-3-(9-xanthyl) propionic acid and 2-amino-2-(3-trans-carboxycyclobutyl)-3-(9-xanthyl)proprionic acid A stirred solution of 5-(cis- and trans-3-carboxycyclobutyl)-5-[(9-xanthyl)methyl]imidazoline-2,4-dione (1.70 g, 4.3 mmol) in 2M sodium hydroxide (21.5 ml, 43 mmol) was heated to 170° C. for 20 hours in a PTFE lined stainless steel pressure vessel. After cooling to room temperature, the yellow solution was diluted with water (10 ml) and acidified with 5M hydrochloric acid (8.5 ml, 45 mmol) to pH4. The precipitated solid was stirred vigorously, filtered, washed with 0.01M hydrochloric acid (20 ml) and dried to give the title product as a tan solid (m.p.>250° C.)

EXAMPLE 2

2-Amino-2-(3-cis-carboxycyclobutyl)-3-(9-xanthyl) propionic acid i) 5-(Cis-3-carboxycyclobutyl)-5-[9-xanthyl)methyl] imidazolidine-2,4-dione The mixture of 5-(cis- and trans-3-carboxycyclobutyl)-5-[(9-xanthyl)methyl]imidazolidine-2,4-dione (80 mg) was recrystallised twice from acetic acid (3 ml) water (1 ml) to give the title product as white needles (m.p. 281° C.) $^1$H NMR ($d_6$-DMSO) δ 12.1 (1H, br s, $CO_2H$), 10.6 (1H, s, CONHCO), 8.39 (1H, s, CONH), 7.05–7.35 (8H, m, ArH), 4.00 (1H, q, $CHAr_2$), 2.76 (1H, quintet, $CHCO_2$), 2.27 (1H, quintet, CHC), 1.55–2.0 (6H, m, 3× $CH_2$).

ii) 2-Amino-2-(3-cis-carboxycyclobutyl)-3-(9-xanthyl) propionic acid

A mixture of 2-amino-2-(3-cis and trans-carboxycyclobutyl)-3-(9-xanthyl)propionic acid (5 mg) was purified by preparative high pressure liquid chromatography using a 250×4.6 mm KR100-5 C18 column and eluting with acetonitrile:water:formic acid 25:75:0.1 containing 10 mM ammonium formate. The eluant for the peak at 10.4 minutes was collected, evaporated to dryness, redissolved in water and freeze-dried to give the title product as a white solid.

EXAMPLE 3

2-Amino-2-(3-cis-carboxycyclobutyl)acetic acid i) Methyl N-formyl-α-(3-methoxycarbonyl cyclobutylidene)glycinate To a suspension of sodium hydride (0.27 g, 6.63 mmol, 60% oil dispersion) in dry tetrahydrofuran (10 ml), was added dropwise with vigorous stirring a solution of 3-methoxycarbonylcyclobutanone (0.707 g, 5.52 mmol) and methyl isocyanoacetate (0.6 g, 6.07 mmol) in dry tetrahydrofuran (20 ml) over 5 minutes. The reaction mixture was stirred at room temperature for 2 hours, cooled to 0° C. and 10% aqueous acetic acid (20 ml) added dropwise. The organic solvent was removed in vacuo and the resulting solution extracted with dichloromethane (3×20 ml). The combined extracts were washed with water, dried over anhydrous magnesium sulphate and evaporated to give an oil. The crude product was purified by flash chromatography, eluting with ethyl acetate-hexane (1:1, 3:2), to give methyl N-formyl-α-(3-methoxycarbonylcyclobutylidene)glycinate as a colourless oil.

ii) Methyl-N-formyl-α-(3-methoxycarbonylcyclobutyl) glycinate

A solution of methyl N-formyl-α-(3-methoxycarbonylcyclobutylidene)glycinate (4.24 mg, 1.87 mmol) in methanol (40 ml) was hydrogenated over 10% palladium-carbon (60 mg) at 65 psi for 1.5 hours. The reaction mixture was filtered through a pad of celite and evaporated to give the title compound as a colourless oil.

iii) 2-Amino-2-(3-cis-carboxycyclobutyl)acetic acid

A solution of methyl-N-formyl-α-(3-methoxycarbonylcyclobutyl)glycinate (200 mg, 0.88 mmol) was heated at reflux for 5 hours in a mixture of tetrahydrofuran (2 ml) and aqueous sodium hydroxide (2M, 2.6 ml). The cooled reaction mixture was neutralised with aqueous hydrochloric acid (2M) and purified by cation-exchange chromatography (Dowex 50 x 8-100. The column was eluted sequentially with water, water-THF 1:1 and water again. The amino acid was finally eluted with water-pyridine 9:1). The pyridine was removed in vacuo and the residue freeze-dried from water to give the title compound as a white solid (mp 229–231° C.)

EXAMPLE 4

2-Amino-2-(3,3-dicarboxycyclobutyl)acetic acid i) Diethyl-3,3-dicarboxycyclobutanone

A stirred mixture of diethyl 3,3-dimethoxycyclobutanedicarboxylate (10.36 g, 39.8 mmol) in acetone (95 ml) and p-toluenesulphonic acid (1.38 g, 8.02 mmol) was heated to 65° C. overnight. Further p-toluenesulphonic acid (200 mg, 1.16 mmol) and acetone (15 ml) were added and the temperature raised to 75° C. for 2 hours. The reaction was cooled to room temperature. The mixture was neutralised with aqueous sodium bicarbonate. Water (15 ml) was added and then extracted with dichloromethane (3×10 ml). The extracts were dried over magnesium sulphate, filtered and evaporated in vacuo to give a brown oil. The crude oil was distilled (bulb-to-bulb) to give diethyl 3,3-dicarboxycyclobutanone as an oil, b.p. 150–155° C./0.1 mm.

ii) Methyl N-formyl-α-(3,3-diethoxycarbonyl cyclobutylidene)glycinate

To a stirred dispersion of sodium hydride (0.24 g, 6 mmol, 60% oil dispersion) in dry THF (10 ml) under an atmosphere of nitrogen was added diethyl 3,3-dicarboxycyclobutanone (1.0 g, 4.67 mmol) in dry THF (10 ml) and methylisocyanoacetate (0.51 g, 5.14 mmol) in dry THF (10 ml) simultaneously. After 3 hours the reaction mixture was cooled in an ice-bath. Aqueous acetic acid (20 ml, 10%) was added. The mixture was concentrated in vacuo and extracted with dichloromethane (3×20 ml), dried over magnesium sulphate, and filtered. The filtrate was evaporated in vacuo, and chromatography on flash silica, eluting with ethyl acetate-:hexane (1:1, 3:1), gave methyl N-formyl-α-(3,3-diethoxycarbonylcyclobutylidene) glycinate as a yellow oil.

iii) Methyl-N-formyl-α-(3,3-diethoxycarbonylcyclo butyl) glycinate

A solution of methyl N-formyl-α-(3,3-diethoxycarbonylcyclobutylidene)glycinate (0.46 g, 1.47 mmol) in ethanol (40 ml) was hydrogenated over 10% palladium-carbon (100 mg) at 65 psi for 24 hours. The reaction mixture was filtered through a pad of celite and evaporated to give a yellow oil.

iv) 2-Amino-2-(3,2-dicarboxycyclobutyl)acetic acid

A stirred mixture of methyl N-formyl-α-(3,3-diethoxycarbonylcyclobutyl)glycinate (404 mg, 1.28 mmol) in ethanol (2 ml) and aqueous sodium hydroxide (3.14 ml, 2M) was heated in a sealed container at 110° C. overnight. The reaction mixture was cooled and neutralised with aqueous hydrochloric acid (2M) and chromatographed on ion exchange resin to give the title product as a white solid (mp 205–209° C.)

EXAMPLE 5

2-Amino-2-(3-trans-carboxycyclobutyl)-3-(9-xanthyl) propionic acid i) 2-Amino-2-(3-trans-ethoxycarbonylcyclobutyl)-3-(9-xanthyl)propionic acid and 2-amino-2-(3-cis-ethoxycarbonylcyclobutyl)-3-(9-xanthyl)propionic acid.

Thionyl chloride (0.41 ml, 5.6 mmol) was added dropwise over 5 minutes to a stirred suspension of cis- and trans-2-amino-2-(3-carboxycyclobutyl)-3-(9-xanthyl)propionic acid (0.51 g, 1.4 mmol) in ethanol (4 ml) cooled in an ice bath. After 16 hours at room temperature, water (0.5 ml) was added with cooling and the mixture filtered. The filtrate was diluted with water (5 ml) and neutralised to pH7 with 2M sodium hydroxide solution. The precipitate was filtered, washed with water and dried to give the title products as a white solid.

ii) 2-Amino-2-(3-trans-ethoxycarbonylcyclobutyl)-3-(9-xanthyl)propionic acid and 3-aza-2-[(9-xanthyl)methyl]-4-oxo-bicyclo[3.1.1]heptane-2-carboxylic acid.

A mixture of cis- and trans-2-amino-2-(3-ethoxy carbonylcyclobutyl)-3-(9-xanthyl)propionic acid (0.45 g, 1.14 mmol) in pyridine (15 ml) was heated under reflux for 24 hours with nitrogen flow through the condenser to allow evaporation of ethanol. The mixture was evaporated to dryness, resuspended in water and evaporated again. The tan coloured residual solid was stirred with water (5 ml) and 2M hydrochloric acid (0.5 ml) and then filtered and dried (0.38 g). The mixture of products were separated by flash chromatography on a silica column eluting sequentially with choloroform:methanol:acetic acid 88:10:2 to give 3-aza-2-[(9-xanthyl]-4-oxo-bicyclo[3.1.1]heptane-2-carboxylic acid (0.26 g) and then with chloroform:methanol:acetic acid 80:10:10 to give 2-amino-2-(3-trans-ethoxycarbonylcyclobutyl)-3-(9-xanthyl)propionic acid (0.11 g) as a white solid.

iii) $^2$-Amino-2-(3-trans-carboxycyclobutyl)-3-(9-xanthyl) propionic acid.

A solution of 2-amino-2-(3-trans-ethoxycarbonylcyclobutyl)-3-(9-xanthyl)propionic acid (0.10 g, 0.25 mmol) in aqueous sodium hydroxide (0.2M, 5 ml) was stirred at room temperature for 1 hour. After filtering, the filtrate was acidified with 2M hydrochloric acid (0.6 ml) to pH3. The thick precipitate was filtered, washed with water and dried to give the title product as a white solid (m.p. 292° C. with decomposition). $^1$H NMR (D$_2$0/NaOD) δ 7.15–7.40 (8H,m ,ArH), 4.12 (1H,t,Ar$_2$CH), 2.71 (1H, septet), 2.52 (1H, quintet), 1.90–2.10 (5H,m), 1.60 (1H,dd).

EXAMPLE 6

2-Amino-2-(3-cis-carboxycyclobutyl)-3-(9-thioxanthyl) propionic acid and 2-amino-2-(3-trans-carboxycyclobutyl)-3-(9-thioxanthyl)propionic acid i) Ethyl 3-oxo-3-(3-phenacyl oxycarbonylcyclobutyl)-2-(9-thioxanthyl)propanate.

Acetic acid (15 ml) was added to a stirred mixture of 9-hydroxythioxanthene (3.10 g, 14.5 mmol) and ethyl-3-oxo-3-(3-phenacyloxycarbonylcyclobutyl)propanate (4.0 g, 12 mmol) in ethanol (15 ml) at room temperature. A clear solution formed and was allowed to stand for 5 days at room temperature. The reaction mixture was filtered and the filtrate evaporated to a brown oil. The oil was dissolved in diethyl ether (100 ml) and washed with saturated aqueous sodium bicarbonate (3×100 ml), brine solution (100 ml) and then dried, filtered and evaporated to a viscous brown oil (6.7 g). Purification by chromatography on flash silica (eluting with chloroform containing 1% methanol increasing to 2% methanol) gave the title product as a brown oil).

ii) Cis- and trans-3-[9-thioxanthyl)methylketo] cyclobutanecarboxylic acid.

A stirred mixture of ethyl 3-oxo-3-(3-phenacyloxycarbonylcyclobutyl)-2-(9-thioxanythl) propanate (5.3 g, 10 mmol) and aqueous sodium hydroxide (2M, 25 ml) in ethanol (25 ml) was heated under reflux for 16 hours. The solution was evaporated to a small volume and then redissolved in water (60 ml). The basic aqueous solution was washed with diethyl ether (2×50 ml) and then acidified to pH1 with 5M hydrochloric acid (20 ml).

The acidic aqueous was extracted with diethyl ether (2×50 ml) and the extracts were then dried, filtered and evaporated to a brown oil (3.6 g). Chromatography on flash silica, eluting with diethyl ether, gave the title products as a yellow waxy solid.

iii) 5-(Cis- and trans-3-carboxycyclobutyl)-5-[(9-thioxanthyl)methyl]imidazolidine-2,4-dione.

A stirred mixture of cis- and trans-3-[(9-thioxanthyl) methylketo]cyclobutane carboxylic acid (2.2 g, 6.5 mmol), potassium cyanide (0.84 g, 13 mmol) and ammonium carbonate (2.50 g, 26 mmol) in ethanol-water (1:1, 20 ml) was heated to 80° C. for 16 hours in a PTFE lined stainless steel pressure vessel. The cold mixture was diluted with water (20 ml) and cautiously acidified by dropwise addition of 5M hydrochloric acid (14 ml). The stirred mixture effervesced and a solid precipitated. After standing for several hours, the solid was filtered, washed with water and dried in vacuo to give the title products.

iv) 2-Amino-2-(3-cis-carboxycyclobutyl-3-(9-thioxanthyl) propionic acid and 2-amino-2-(3-trans-carboxycyclobutyl)-3-(9-thioxanthyl)propionic acid.

A stirred solution of 5-(cis-and trans-3-carboxy cyclobutyl)-5-[(9-thioxanthyl)methyl] imidazolidine- 2,4-dione (2.0 g, 4.9 mmol) in 2M sodium hydroxide (25 ml) was heated to 180° C. for 16 hours in a PTFE lined stainless steel pressure vessel. After cooling to room temperature, the mixture was filtered and the filtrate washed with ethyl acetate (25 ml). The aqueous solution was acidified to pH5 to 6 with 5M hydrochloric acid (4 ml) and then to pH4 with acetic acid (10 ml). The precipitated solid was stirred vigorously, filtered, washed with water and dried to give an off-white solid. The solid was suspended with stirring in water (40 ml) and ethyl acetate (20 ml) and then filtered to give the title product as a white solid (m.p. 233–248° C.)

EXAMPLE 7

2-Amino-2-(3-cis-carboxycyclobutyl)-3-(9-hydroxy-10-oxido-9-thioxanthyl)propionic acid and 2-amino-2-(3-trans-carboxycyclobutyl-3-(9-hydroxy-10-oxido-9-thioxanthyl) propionic acid Hydrogen peroxide solution 30% w/v (0.23 ml, 2 mmol) was added to a stirred suspension of 5-(cis- and trans-3-carboxycyclobutyl)-5-[9-thioxanthyl)methyl]imidazolidine-2,4-dione (0.21 g, 0.51 mmol) in acetic acid (2 ml) at room temperature. After 24 hours the mixture was heated to 50° C. for 16 hours and then the clear solution evaporated. The residual solid was suspended with stirring in water (2 ml) diethyl ether (1 ml) and then filtered and dried to give an off-white solid of 5-(cis- and trans-3-carboxycyclobutyl)-5-[10,10-dioxido-9-thioxanthyl) methyl]imidazolidine-2,4-dione (m.p. 282–4° C.)

A stirred solution of the imidazolidine-2,4-dione (0.14 g, 0.32 mmol) in sodium hydroxide 1M (4 ml) was heated to 170° C. for 24 hours in a PTFE lined stainless steel pressure vessel. The cold mixture was acidified to pH-3 with 5M hydrochloric acid (0.9 ml) and a small amount of precipitate filtered. The filtrate was chromatographed on ion exchange (Dowex 50X8-100 resin) eluting sequentially with water, water-THF 1:1, water and 10% water-pyridine. Fractions collected after the water-pyridine elution were combined, evaporated, redissolved in water (3 ml) and freeze dried to give the title product as a white solid (m.p. 166–7° C.).

EXAMPLE 8

2-Amino-2-(3-cis-carboxycyclobutyl)-3-(10,10-dioxido-9-thioxanthyl)propionic acid Hydrogen peroxide 30% w/v (0.11 ml) was added to a stirred suspension of cis- and trans-2-amino-2-(3-carboxycyclobutyl)-3-(9-thioxanthyl)propionic acid (0.1 g, 0.26 mmol) in acetic acid (2 ml) at room temperature. The suspension was heated to 50° C. for 16 hours and then cooled to room temperature. The white solid was filtered to give the title product (m.p. 237–8° C. with decomposition).

EXAMPLE 9

2-Amino-2-(3-trans-carboxycyclobutyl)-3-(9-thioxanthyl) propionic acid

A mixture of 2-amino-2-(3-cis and trans-carboxy cyclobutyl)-3-(9-thioxanthyl)propionic acid (10×5 mg portions) was purified by preparative high pressure liquid chromatography using a 100×4.6 mm 7μ Hypercarb column eluting with acetonitrile:water:formic acid 35:65:0.2. The eluants for the peak at 23.4 minutes were collected, evaporated to dryness, redissolved in 3M hydrochloric acid, filtered and the filtrate evaporated. The residual solid was resuspended in water and freeze dried to give the title product as a white solid.

EXAMPLE 10

2-Amino-2-(3-cis-carboxycyclobutyl)-3-(9-thioxanthyl) propionic acid

The title compound was obtained as a white solid (5.3 mg) by the preparative HPLC method described in Example 9 collecting the eluants for the peak at 28 minutes.

EXAMPLE 11

2-Amino-2-(3-cis-carboxycyclobutyl)-3-(2,7-dibromo-9-xanthyl)propionic acid and 2-amino-2-(3-trans-carboxycyclobutyl)-3-(2,7-dibromo-9-xanthyl)propionic acid A solution of bromine in acetic acid (0.54 ml, 1M solution) was added dropwise over 15 minutes to a stirred suspension of 2-amino-2-(3-cis and trans-carboxycyclobutyl)-3-(9-xanthyl)propionic acid (0.10 g, 0.27 mmol) in acetic acid (2 ml) at room temperature. After 1.5 hours the mixture was filtered and the filtrate diluted with water (2 ml). The solution was neutralised with 2M sodium hydroxide (0.25 ml, 0.5 mmol) and the precipitate stirred. The suspension was filtered and dried to give the title products as a tan coloured solid (m.p. 241–6° C. with decomposition).

EXAMPLE 12

2-Amino-2-(3-cis-carboxycyclobutyl)-4,4-diphenylbutanoic acid i) Diethyl 3,3-diphenylpropylphosphonate Diethyl 3,3-diphenylpropylbromide (43.0 g, 0.156 mol) and triethyl phosphite (51.9 g, 0.31 mol) was heated to 150° C. for 20 hours in a flask equipped with nitrogen flow through and an air condenser. Extra triethyl phosphite (20 ml) was added and heating continued to 160° C. for 3 hours. The yellow reaction solution was distilled, collecting several fractions to give the title product as a pale yellow liquid (b.p. 162–176° C. at 0.08 mbar) that crystallised on standing.

ii) Diethyl 3,3-diphenyl-1-(methylthio)propylphosphonate

A solution of n-butyl lithium (2.5M in n-hexane, 132 ml, 33 mmol) was added dropwise over 10 minutes to a stirred solution of diethyl 3,3-diphenylpropylphosphonate (9.96 g, 30 mmol) in dry tetrahydrofuran (100 ml) cooled to −60° C. under nitrogen atmosphere. After 20 minutes at −60° C. a solution of dimethyl disulphide (2.96 ml, 33 mmol) in dry tetrahydrofuran (5 ml) was added in one portion turning the solution colour from orange to pale yellow immediately. After 30 minutes at −60° C., water (200 ml) was added and the mixture extracted with diethyl ether (2×100 ml). The ether extracts were washed with saturated aqueous sodium bicarbonate (2×100 ml), brine solution (100 ml), dried, filtered and evaporated to a yellow oil (13 g). Chromatography on flash silica eluting with diethyl ether gave the title product as a colourless oil.

iii) Diethyl 3-(3,3-diphenyl-1-(methylthio)propenyl) cyclobutane-1,1-dicarboxylate A solution of n-butyl lithium (2.5M in hexane, 4 ml, 10 mmol) was added dropwise to a stirred solution of diethyl 3,3-diphenyl-1-(methylthio)propylphosphonate (3.8 g, 10 mmol) in dry tetrahydrofuran (40 ml) under nitrogen cooled to −60° C. The mixture was allowed to warm to −20° C. for 5 minutes than recooled to 60° C. After 30 minutes a solution of diethyl 3-oxo-cyclobutane-1,1-dicarboxylate (2.14 g, 10 mmol) in dry tetrahydrofuran (5 ml) was added dropwise. After 30 minutes at −60° C. the mixture was allowed to warm to room temperature and then poured onto water (100 ml). The mixture was extracted with diethyl ether (100 ml) and the extracts washed with brine solution, dried, filtered and evaporated to give a pale yellow oil (5 g). Chromatography on flash silica eluting with diethyl ether-:petroleum ether 40:60 gave the title product as a colourless oil.

iv) Diethyl 3-(3,3-diphenyl-1-oxopropanylcyclobutane-1,1-dicarboxylate.

A stirred mixture of diethyl 3-[3,3-diphenyl-1-(methylthio)propenyl]cyclobutane-1,1-dicarboxylate in dioxan (20 ml) and 2M hydrochloric acid (4 ml) was treated to 100° C. for 1 hour. The cooled mixture was diluted with water (50 ml) and extracted with diethyl ether (50 ml). The ether extracts were dried, filtered and evaporated to an oily solid (1.68 g). Recrystallisation from ethanol (5 ml) gave the title product as white needles (m.p. 75° C.) 1H NMR (CDCl$_3$) δ 7.15–7.30 ($^{10}$H, m, ArH), 4.60 ($^1$H,t,CHPh$_2$), 4.13 and 4.20 ($^4$H, 2× q, OCH$_2$), 3.19 ($^1$H, m, COCH), 3.12 ($^2$H, d, COCH$_2$), 2.55 and 2.60 ($^4$H, s and d, 2× CH$_2$), 1.25 and 1.27 ($^6$H, 2× t, CH$_3$).

v) 5-[3,3-Di(ethoxycarbonyl)cyclobutyl]-5-(2,2-diphenylethyl)imidazolidine-2,4-dione.

A stirred mixture of diethyl 3-(3,3-diphenyl-1-oxopropanylcyclobutane-1,1-dicarboxylate (0.70 g, 1.7 mmol), potassium cyanide (0.22 g, 3.4 mmol) and ammonium carbonate (0.65 g, 6.8 mmol) in ethanol-water (1:1, 5 ml) was heated to 80° C. for 16 hours in a PTFE lined stainless steel pressure vessel. The cold mixture was diluted with water (15 ml) and cautiously acidified with 5M hydrochloric acid. The mixture was extracted with ethyl acetate (20 ml) and the extracts washed with brine solution (20 ml), dried, filtered and evaporated to give the title product as a viscous glass.

vi) 5-(3,3-Dicarboxycyclobutyl)-5-(2,2-diphenylethyl) imidazolidine-2,4-dione

A stirred mixture of 5-[3,3-di(ethoxycarbonyl) cyclobutyl]-5-(2,2-diphenylethyl)imidazolidine-2,4-dione (1.7 mmol) in 1M sodium hydroxide (17 ml) was heated to 70° C. for 2 hours. The cooled solution was filtered and the filtrate acidified with 5M hydrochloric acid (4 ml). The mixture was extracted with diethyl ether (30 ml) ethanol (3 ml) to give the title product as a white foam.

vii) 5-(3-Cis-carboxycyclobutyl)-5-(2,2-diphenylethyl) imidazolidine-2,4-dione and 5-(3-trans-carboxycyclobutyl)-5-(2,2-diphenylethyl) imidazolidine-2,4-dione.

Solid 5-(3,3-dicarboxoycyclobutyl)-5-(2,2-diphenyl ethyl)imidazolidine-2,4-dione (0.7 g) was heated to 180–200° C. for 40 minutes. On cooling, the title products solidified.

viii) 2-Amino-2-(3-cis-carboxycyclobutyl)-4,4-diphenylbutanoic acid

A solution of 5-(3-cis and trans-carboxycyclobutyl)-5-(2, 2-diphenylethyl)imidazolidine-2,4-dione (0.3 g,0.8 mmol in 2M sodium hydroxide (6 ml) was heated to 150° C. for 48 hours in a PTFE lined stainless steel pressure vessel. After cooling, the mixture was filtered and the filtrate was acidified to pH5 with 5M hydrochloric acid (2.2 ml). The precipitate was cooled and filtered, washed with water and dried to give the title product.

EXAMPLE 13

2-Amino-2-(3,3-dicarboxycyclobutyl)-4,4-diphenylbutanoic acid

A solution of 5-(3,3-dicarboxycyclobutyl)-5-(2,2-diphenylethyl)imidazolidine-2,4-dione (0.21 g, 0.5 mmol) in 2M sodium hydroxide (4 ml) was heated to 150° C. for 4 days in a PTFE lined stainless steel pressure vessel. After cooling, the mixture was filtered and the filtrate acidified with 5M hydrochloric acid (2 ml). The precipitate was cooled and filtered, washed with water and dried to give the title product (m.p. 182–185° C. with effervescence). $^1$H NMR (D$_2$O/NaOH) δ 7.21–7.50 (10H, m)), 4.06 (1H, dd), 2.44–2.63 (2H, m), 2.11–2.38 (5H, m).

EXAMPLE 14

(−)-2-Amino-2-(3-cis-carboxycyclobutyl)-3-(9-thioxanthyl) propionic acid

A solution of L-lysine (0.38 g, 2.61 mmol) and 2-amino-2-(3-cis and 3-trans-carboxycyclobutyl)-3-(9-thioxanthyl) propionic acid in water (20 ml) was diluted with ethanol (20 ml) and then filtered to remove trace insolubles. The filtrate was diluted with ethanol (120 ml) and allowed to crystallise at room temperature and then in a fridge. The thick suspension was filtered and the gelatinous solid washed with ethanol and dried to give the salt (0.48 g). Recrystallised by dissolving in warm water (20 ml) and then diluting with ethanol (120 ml). After allowing to crystallise the salt was filtered and dried (0.18 g). The salt was dissolved in water (15 ml) and acidified with 2M hydrochloric acid (1.5 ml). After stirring, the thick mixture was filtered and the solid washed with water (10 ml) by resuspending to give the title product as an off-white powder ('H NMR (D$_2$O/NaOD). δ m.p. 228–230° C. with effervescence). $^1$H NMR (D$_2$O/NaOD) δ 7.28–7.55 (m, 8H), 4.36 (t, 1H), 2.68 (quintet, 1H), 2.27 (m, 1H), 1.75–2.00 (m, 6H).

EXAMPLE 15

(+)-2-Amino-2-(3-cis-carboxycyclobutyl)-3-(9-thioxanthyl) propionic acid

A solution of D-lysine monohydrate (0.43 g, 2.61 mmol) and 2-amino-2-(3-cis and 3-trans-carboxycyclobutyl)-3-(9-thioxanthyl)propionic acid in water (20 ml) was diluted with ethanol (20 ml) and then filtered to remove trace insolubles. The filtrate was diluted with ethanol (120 ml) and allowed to crystallise at room temperature and then in a fridge. The thick suspension was filtered and the gelatinous solid washed with ethanol and dried to give the salt (0.48 g). Recrystallised by dissolving in warm water (20 ml) and then diluting with ethanol (120 ml). After allowing to crystallise, the salt was filtered and dried (0.14 g). The salt was dissolved in water (12 ml) and acidified with 2M hydrochloric acid (1.2 ml). After stirring, the thick mixture was filtered and the solid washed with water (10 ml) by resuspending to give the title product as a light grey powder (38 mg).

EXAMPLE 16

Cis-2-amino-2-(3-carboxycyclobutyl)-3-naphthylpropanoic acid i) Benzyl methyl 3-methoxycarbonylcyclo butylidenemalonate To a suspension of titanium tetracholoride tetrahydrofuran complex (85 g, 0.26 mol) in dry tetrahydrofuran (400 ml) stirred at −10° C. under a nitrogen atmosphere was added a solution of methyl 4-oxocyclobutanecarboxylate (15 g, 0.13 mol) and benzyl methylmalonate (28.03 g, 0.13 mol) in dry tetrahydrofuran (100 ml) dropwise over a period of 10 minutes. A solution of dry pyridine (42 ml) in dry tetrahydrofuran (100 ml) was then added at a rate that maintained the reaction temperature below 0° C. The resulting suspension was stirred at room temperature overnight, followed by addition of ice cold water (400 ml) and separation of the organic phase. The aqueous phase was extracted with diethyl ether (2×150 ml) and the combined organic phases washed with aqueous hydrochloric acid (2M, 100 ml) and brine solution (100 ml). The organic phase was dried, filtered and evaporated to give a red oil (43.4 g). Chromatography on flash silica eluting with hexane-diethylether (75:25) gave the title compound as a colourless oil.

ii) Benzyl methyl cis-3-methoxycarbonylcyclobutylmalonate

Sodium borohydride (4.28 g, 0.11 mol) was added portionwise to a stirred solution of benzyl methyl 3-methoxycarbonylcyclobutylidenemalonate (30 g, 0.09 mol) in dry tetrahydrofuran (200 ml) cooled to 0° C. The cooling bath was then removed and after 20 minutes water (300 ml) was added. The mixture was extracted with diethyl ether (3×200 ml) and the combined extracts washed with brine solution. The organic phase was dried, filtered and evaporated to a colourless oil (27.0 g). Chromatography on flash silica eluting with hexane-ether (9:1 then 8:2 then 7:3) gave the title compound as a colourless oil).

iii) Benzyl cis-2-methoxycarbonyl-2-(3-methoxycarbonylcyclobutyl)-3-naphthylpropanoate To a stirred suspension of potassium t-butoxide (0.44 g, 3.93 mmol) in dry tetrahydrofuran (20 ml) cooled to 0° C. under a nitrogen atmosphere was added dropwise a solution of benzyl methyl cis-3-methoxycarbonylcyclobutylmalonate (1.25 g, 3.9 mmol) in dry tetrahydrofuran (20 ml) followed by dropwise addition of 1-(bromomethyl)naphthalene (2.58 g, 11.7 mmol) in dry toluene (15 ml). Stirring was continued at 0° C. for 4 hours, aqueous hydrochloric acid (2M, 15 ml) was then added and the mixture extracted with diethyl ether. The organic phase was dried, filtered and evaporated to an oil (2.5 g). The oil was dissolved in dichloromethane and filtered through a pad of flash silica, the solvent was removed and the resulting oil (2.0 g) purified by chromatography on silica using a Biotage Flash 40 eluting with dichloromethane to give the title compound as a colourless oil.

iv) Cis-2-methoxycarbonyl-2-(3-methoxycarbonyl cyclobutyl)-3-naphthylpropanoic acid.

A solution of benzyl cis-2-methoxycarbonyl-2-(3-methoxycarbonylcyclobutyl)-3-naphthylpropanoate (0.53 g, 1.15 mmol) in ethyl acetate (30 ml) was hydrogenated over 10% palladium-carbon (0.06 g) at 65 psi for 20 hours. The reaction mixture was filtered through a pad of celite and evaporated to a brown oil (0.4 g). Chromatography on flash silica eluting with diethyl ether-hexane (3:2) and then diethyl ether gave the title compound as an off-white gum.

v) Methyl cis-2-isocyanato-2-(3-methoxycarbonyl cyclobutyl)-3-naphthylpropanoate A mixture of cis-2-methoxycarbonyl-2-(3-methoxy carbonylcyclobutyl)-3-naphthylpropanoic acid (0.25 g, 0.68 mmol), dry triethylamine (72 mg, 0.71 mmol) and diphenylphosphonic azide (0.2 g, 0.71 mmol) in dry toluene (10 ml) was heated with stirring at 80° C. under a nitrogen atmosphere for 20 hours. After cooling the reaction mixture, water was added and the organic phase separated. The aqueous phase was extracted with diethyl ither and the combined organic phases dried, filtered and evaporated to an oil. The crude product was purified by chromatography on flash silica eluting with diethyl ether-hexane (1:1) to give the title compound as a white solid.

vi) Cis-2-amino-2-(3-carboxycyclobutyl)-3-naphthylpropanoic acid

A stirred solution of methyl cis-2-isocyanate-2-(3-methoxycarbonylcyclobutyl)-3-naphthylpropanoate (0.14 g, 0.38 mmol) in a mixture of water (15 ml) and tetrahydrofuran (5 ml) treated with aqueous sodium hydroxide (2M, 1.14 ml) was heated at reflux. After 7 hours, the reaction mixture was cooled and acidified with acetic acid. The resulting fine suspension was chromatographed on ion exchange resin to give the title compound as a white powder (88 mg, m.p. 189–191° C.) $^1$H NMR ($D_2O$/NaOD) δ 8.23 (d), 7.92–7.95 (m), 7.83 (d), 7.43–7.61 (m), 3.33 (dd), 2.70–2.85 (m), 1.90–2.13(m).

EXAMPLE 17

Cis-2-amino-2-(3-carboxycyclobutyl)-3-(9-anthracenyl) propanoic acid i) Benzyl cis-2-methoxycarbonyl-2-(3-methoxycarbonylcyclobutyl)-3-(9-anthracenyl)propanoate.

A solution of 9-(bromomethyl)anthracene (1.68 g, 6.2 mmol) in dry tetrahydrofuran (20 ml) was added to a mixture of potassium-t-butoxide (0.66 g, 5.91 mmol) and benzyl methyl cis-3-methoxycarbonylcyclobutyl malonate (1.8 g, 5.63 mmol) following the procedure described in Example 16 (iii). The reaction mixture was kept at 0° to 5° C. for 22 hours followed by work up as previously described and chromatography on flash silica eluting with hexane-diethyl ether (3:2) to give the title compound as a yellow oil.

ii) Cis-2-methoxycarbonyl-2-(3-methoxycarbonylcyclobutyl)-3-(9-anthracenyl)propanoic acid.

A solution of benzyl cis-2-methoxycarbonyl-2-(3-methoxycarbonylcyclobutyl)-3-(9-anthracenyl)propanoate (1.23 g,2.41 mmol) in a mixture of methanol (40 ml) and ethyl acetate (20 ml) was hydrogenated over 10% palladium-carbon (0.14 g) at 10 psi for 2 days. The reaction mixture was filtered through a pad of celite and evaporated to a gum (1.1 g). The crude mixture was purified by chromatography on flash silica eluting with hexane-ethylacetate (3:2) to give the title compound as an oil.

iii) Methyl cis-2-isocyanato-2-(3-methoxycarbonyl cyclobutyl)-3-(9-anthracenyl)propanoate.

A mixture of cis-2-methoxycarbonyl-2-(3-methoxycarbonylcyclobutyl)-3-(9-anthracenyl)propanoic acid (0.15 g, 0.36 mmol), dry triethylamine (37 mg, 0.37 mmol) and diphenylphosphonic azide (103 mg, 0.37 mmol) in dry toluene (5 ml) was heated with stirring at 100° C. under a nitrogen atmosphere for 5 hours. Work up and chromatography eluting with hexane-diethyl ether (17:8) as described in Example 16 (v) gave the title compound as a white solid.

iv) Cis-2-amino-2-(3-carboxycyclobutyl)-3-(9-anthracenyl) propanoic acid.

Methyl cis-2-isocyanato-2-(3-methoxycarbonyl cyclobutyl)-3-(9-anthracenyl)propanoate (65 mg, 0.16 mmol) was treated with aqueous sodium hydroxide and the reaction worked up following the procedure described in Example 16 (vi) to give the title compound as a pale yellow solid (m.p. 213–216° C.), $^1$H NMR ($D_2O$/NaOD) δ 8.42(s), 8.35(d), 8.06(s), 8.02(d),7.50–7.58 (m), 3.87 (dd), 2.70–2.92 (m), 1.88–2.06(m)

EXAMPLE 18

2-Amino-2-(trans-3-carboxyl-1-phenylcyclobutyl)acetic acid i) Benzyl methyl trans-3-methoxycarbonyl-1-phenyl cyclobutylmalonate.

To a suspension of cuprous cyanide (0.84 g, 9.43 mmol) in dry diethyl ether (70 ml) stirred at –70° C. under a nitrogen atmosphere was added a solution of phenyllithium in cyclohexane-diethyl ether (7.3, 1.8M, 10.1 ml) dropwise. The suspension was allowed to warm to −30° C. becoming a red solution and then cooled to −60° C. A mixture of benzyl methyl 3-methoxycarbonylcyclobutylidene malonate (2.0 g, 6.29 mmol), dry triethylamine (1.28 g, 12.6 mmol) and trimethylsilyl chloride (1.37, 12.6 mmol) in dry diethyl ether (10 ml) was then added dropwise. The resulting yellow suspension was allowed to warm to 20° C. and after 1.5 hours a solution of aqueous saturated ammonium chloride (20 ml) and aqueous ammonia (5 ml) was added and stirring continued to give a solution. The organic layer was separated and washed with water and brine solution, dried, filtered and evaporated to a red oil. Chromatography on flash silica eluting with hexane-diethyl ether (3:2) gave the title compound as a colourless oil.

ii) 2-Methoxycarbonyl-2-(trans-3-methoxycarbonyl-phenylcyclobutyl)acetic acid.

A solution of benzyl methyl trans-3-methoxycarbonyl-1-phenylcyclobutyl malonate (0.79 g, 2.0 mmol) in methanol (35 ml) was hydrogenated over 10% palladium-carbon (100 mg) at 65 psi for 1.5 hours. The reaction mixture was filtered through a pad of celite and evaporated to give the title compound as a colourless oil.

iii) Methyl 2-benzyloxyacetamido-2-(trans-3-methoxycarbonyl-1-phenylcyclobutyl)acetate A mixture of 2-methoxycarbonyl-2-(trans-3-methoxycarbonyl-1-phenylcyclobutyl)acetic acid (0.6 g, 1.94 mmol), dry triethylamine (0.21 g, 2.04 mmol) and diphenylphosphonic azide (0.56 g, 2.04 mmol) in dry toluene (10 ml) was heated with stirring at 100° C. under a nitrogen atmosphere. After 3 hours, benzyl alcohol (0.22 g, 2.04 mmol) was added and heating at 100° C. continued overnight. The cooled reaction mixture was diluted with water and extracted with diethyl ether. The extract was washed with water and brine solution, dried, filtered and evaporated to an oil. The crude product was purified by chromatography on flash silica eluting with hexane-diethylether (3:2) to give a colourless oil.

iv) 2-Benzyloxyacetamido-2-(trans-3-carboxy-1-phenyl cyclobutyl) acetic acid.

A solution of methyl 2-benzyloxyacetamido-2-(trans-3-methoxycarbonyl-1-phenylcyclobutyl)acetate (0.36 g, 0.88 mmol) in tetrahydrofuran (6 ml) was treated with aqueous sodium hydroxide (2M, 1.77 ml) and heated with stirring at reflux overnight. The cooled reaction mixture was diluted with water and washed with a mixture of hexane-diethyl ether (3:2, 2×10 ml). The aqueous phase was acidified with aqueous hydrochloric acid and extracted three times with ethyl acetate. The combined extracts were dried, filtered and evaporated to a colourless gum.

v) 2-Amino-2-(trans-3-carboxy-1-phenylcyclobutyl)acetic acid

A solution of 2-benzyloxyacetamido-2-(trans-3-carboxy-1-phenylcyclobutyl)acetic acid (0.18 g, 0.46 mmol) in methanol (20 ml) and water (10 ml) was hydrogenated over 10% palladium-carbon (30 mg) at 65 psi. After 3 hours, the reaction mixture was filtered through a pad of celite and evaporated to white solid. The solid was suspended in water, filtered and then washed with water and cold diethyl ether to give the title compound (44 mg, m.p. 189–191° C.) $^1$H NMR (D$_2$0/NaOD) δ 7.38–7.54(m), 3.52(s), 2.63–2.82(m), 2.42–2.53(m).

EXAMPLE 19

Cis-2-amino-2-(3-carboxycyclobutyl)-4-(10,10-dioxido-9-thioxanthyl)butanoic acid i) 9 Hydroxy-9-vinyl thioxanthane-10,10-dioxide To a stirred solution of thioxanthone-10,10-dioxide (4.0 g, 16.37 mmol) in dry tetrahydrofuran (100 ml) cooled to −20° C. was added a solution of vinylmagnesium chloride in tetrahydrofuran(15%, 11.4 ml) dropwise. The purple solution was then heated at 70° C. for 18 hours, cooled and aqueous saturated ammonium chloride added. The mixture was extracted with ethyl acetate and the organic phase dried and filtered, on concentration in vacuo crystals separated and were collected. A second crop from the filtrate gave a combined yield of 1.06 g for the title compound.

ii) 9-(2-Bromoethylidenyl)thioxanthene-10,10-dioxide

A suspension of 9-hydroxy-9-vinylthioxanthene-10,10-dioxide (0.95, 3.49 mmol) in acetic acid (5 ml) was treated with hydrogen bromide in acetic acid (30%, 1 ml) and heated with stirring at 90° C. for 10 minutes to give a red solution. The cooled reaction mixture was poured into ice cold water and extracted with ethyl acetate. The extract was washed with aqueous sodium carbonate (2M), water and brine solution, dried, filtered and evaporated to a yellow foam to give the title compound.

iii) Benzyl cis-2-methoxycarbonyl-2-(3-methoxycarbonyl cyclobutyl) -4-(10,10-dioxidothioxanth-9-ylidenyl) butanoate.

A mixture of potassium-t-butoxide (0.38 g, 3.43 mmol) and benzyl methyl cis-3-methoxycarbonylcyclobutyl malonate (1.04 g, 3.26 mmol) was reacted with 9-(2-bromoethylidenyl)thioxanthene-10,10-dioxide (1.15 g, 3.43 mmol) in dry tetrahydrofuran (40 ml) and worked up as described in Example 17 (i). The crude product was purified by chromatography on flash silica eluting with diethyl ether-hexane (1:1 then 3:2) to give the title compound as a white foam.

iv) Cis-2-methoxycarbonyl-2-(3-methoxycarbonylcyclobutyl) 4-(10,10-dioxido-9-thioxanthyl)butanoic acid.

A solution of benzyl cis-2-methoxycarbonyl-2-(3-methoxycarbonylcyclobutyl)-4-(10,10-dioxidothioxanth-9-ylidenyl)butanoate (1.17 g, 2.08 mmol) in methanol (100 ml) was hydrogenated over 5% palladium-carbon (0.15 g) at 65 psi for 5 hours. The reaction mixture was filtered through a pad of celite and evaporated to give the title compound as an oil.

v) Methyl cis-2-isocyanato-2-(3-methoxycarbonyl cyclobutyl)-4-(10,10-dioxido-9-thioxanthyl)butanoate.

A mixture of cis-2-methoxycarbonyl-2-(3-methoxy carbonylcyclobutyl)-4-(10,10-dioxido-9-thioxanthyl) butanoic acid (0.87 g, 1.79 mmol), triethylamine (0.19 g, 1.88 mmol) and diphenyl phosphonic azide (0.33 g, 1.88 mmol) in toluene (30 ml) were heated at 75° C. and worked up following the procedure described in Example 17(iii). The crude product was purified by chromatography on flash silica eluting with diethyl ether-hexane (7:3) to give a colourless oil and then crystallised from diethyl ether to give the title compound.

vi) Cis-2-amino-2-(3-carboxycyclobutyl)-4-(10,10-dioxido-9-thioxanthyl)butanoic acid.

A suspension of methyl cis-2-isocyanato-2-(3-methoxcarbonylcyclobutyl)-4-(10,10-dioxido-9-thioxanthyl)butanoate (0.23 g, 0.48 mmol) in aqueous hydrochloric acid (5M, 2 ml) was heated with stirring at 105° C. for 3 days in a PTFE lined stainless steel pressure vessel. The cooled solution was evaporated and the resulting solid re-dissolved in water. Evaporation of the solution gave the title compound as a white foam (205–208° C.) $^1$H NMR (D$_2$0/NaoD) δ 7.96(t), 7.63(t), 7.48–7.57(m), 2.75(m), 2.38 (m), 1.58–2.05(m), 1.25–1.38(m).

EXAMPLE 20

2-Amino-2-(3-cis-carboxycyclobutyl)-3-(2-chloro-9-thioxanthyl)propionic acid and 2-amino-2-(3-transcarboxycyclobutyl)-3-(2-chloro-9-thioxanthyl) propionic acid i) Ethyl 2-(2-chloro-9-thioxanthyl)-3-oxo-3-(3-phenacyloxycarbonylcyclobutyl)propanoate 2-Chloro-9-hydroxythioxanthene (0.72 g, 2.89 mmol) was allowed to react with ethyl 3-oxo-3-(3-phenacyloxycarbonylcyclobutyl)propanoate (0.8 g, 2.41 mmol) in acetic acid (4 ml) and ethanol (4 ml) for 4 days and then heated at 60° C. for 4 hours. Worked up following procedure described in Example 6(i) to give a yellow oil. The crude product was purified by chromatography on flash silica eluting with chloroform then chloroform-methanol (99.5:0.5 then 99:1) to give the title compound as an oil.

ii) 3-[(2-Chloro-9-thioxanthyl)methylketo]cyclobutane carboxylic acid.

Ethyl 2-(2-chloro-9-thioxanthyl)-3-oxo-3-(3-phenacyloxycarbonylcyclobutyl)propanoate (0.64 g, 1.14 mmol) in ethanol (5 ml) was treated with aqueous sodium hydroxide (2M, 3 ml) following the procedure described in Example 6(ii). The resulting yellow oil (0.68 g) crystallised from diethyl ether-hexane (3:2) to give the title compound (0.12 g). The filtrate was evaporated and the crude purified by chromatography on flash silica eluting with diethyl ether-hexane (4:1) to give further title compounds as a powder.

iii) 5-(3-Carboxycyclobutyl)-5-(2-chloro-9-thioxanthyl methyl)imidazolidine-2,4-dione A stirred mixture of 3-[(2-chloro-9-thioxanthyl) methylketo]cyclobutane carboxylic acid (0.22 g, 0.59 mmmol), potassium cyanide (77 mg, 1.18 mmol) and ammonium carbonate (0.23 g, 2.36 mmol) in ethanol-water (1:1, 5 ml) was heated and then worked up following the procedure described in Example 6 (iii). The acidified reaction mixture was extracted with ethyl acetate (5×20 ml) and the combined extracts dried, filtered and evaporated to a yellow foam (0.40 g). The crude product was purified by chromatography on flash silica eluting with chloroform-methanol-aceticacis (90:10:1) to give the title compound as an off-white foam.

iv) 2-Amino-2-(3-cis-carboxycyclobutyl)-3-(2-chloro-9-thioxanthyl)propionic acid and 2-amino-2-(3-transcarboxycyclobutyl)-3-(2-chloro-9-thioxanthyl) propionic acid.

5-(3-Carboxycyclobutyl)-5-(2-chloro-9-thioxanthylmethyl)imidazolidine-2,4-dione (0.23 g, 0.52 mmol) was treated with aqueous sodium hydroxide (1M, 5 ml) and worked up following the procedure described in Example 6(iv) to give a red powder (78 mg). The powder was dissolved in water (4 ml) by addition of aqueous sodium hydroxide (2M, 0.4 ml) and then acidified with acetic acid (1 ml). The precipitate was filtered, washed with water and dried. The precipitate was then stirred as a suspension in water (2 ml) and ethyl acetate (2 ml) for 1 hour, filtered and dried to give the title compound as an orange solid (m.p. 244–246° C.). $^1$HNMR (D$_2$0/NaOD) δ 7.12–7.44(m), 4.23 (dd) 2.60–2.80(m), 2.45–2.55(m), 2.19–2.32(m), 1.76–2.10 (m).

EXAMPLE 21

2-Amino-2-(3-cis-carboxycyclobutyl)-3-(2,4-diethyl-9-thioxanthyl)propionic acid and 2-amino-2-(3-transcarboxycyclobutyl-3-(2,4-diethyl-9-thioxanthyl)propionic acid i) 2,4-Diethyl-9-hydroxythioxanthene To a stirred solution of 2,4-diethyl-9H-thioxanthen-9-one (20 g, 74.5 mmol) in methanol (400 ml) cooled in an ice bath was added sodium borohydride (8 g, 0.2 mole) portionwise. After 1 hour at room temperature, water (100 ml) was added to the reaction mixture and the precipitate collected and washed with water to give the title compound as a white solid (20 g).

ii) Ethyl 2-(2,4-diethyl-9-thioxanthyl)-3-oxo-3-(3-phenacyloxycarbonylcyclobutyl)propanoate.

2,4-Diethyl-9-hydroxythioxanthene (0.62 g, 2.89 mmol) was allowed to react with ethyl 3-oxo-3-(3-phenacyloxycarbonylcyclobutyl)propanoate (0.8 g, 2.41 mmol) in acetic acid (5 ml) and ethanol (5 ml) for 3 days and worked up following the procedure described in Example 6(i). The crude product was purified by chromatography on flash silica eluting with diethyl ether-hexane (1:4) to give the title compound.

iii) 3-[(2,4-Diethyl-9-thioxanthyl)methylketo]cyclobutane carboxylic acid

Ethyl 2-(2,4-diethyl-9-thioxanthyl)-3-oxo-(3-phenacyloxycarbonylcyclobutyl)propanoate (0.89 g, 1.52 mmol) in ethanol (5 ml) was treated with aqueous sodium hydroxide (2M, 3 ml) and the reaction worked up following the procedure described in Example 6(ii) to give the title compound as a brown oil.

iv) 5-(3-Carboxycyclobutyl)-5-(2,4-diethyl-9-thioxanthylmethyl)imidazolidine-2,4-dione A stirred mixture of 3-[2,4-diethyl-9-thioxanthyl) methylketo]cyclobutane carboxylic acid (0.52 g, 1.35 mmol), potassium cyanide (0.18 g, 2.69 mmol) and ammonium carbonate (0.52 g, 5.38 mmol) in ethanol- water (1:1, 10 ml) was heated and then worked up following the procedure described in Example 6(iii). The acidified reaction mixture was extracted with ethyl acetate (5×20 ml) and the combined extracts dried, filtered and evaporated to a foam (0.63 g). The crude product was purified by chromatography on flash silica eluting with chloroform-methanol-acetic acid (90:10:1) to give the title compound as a white foam.

v) 2-Amino-2-(3-cis-carboxycyclobutyl)-3-(2,4-diethyl-9-thioxanthyl)propionic acid and 2-amino-2-(3-transcarboxycyclobutyl-3-(2,4-diethyl-9-thioxanthyl)propionic acid.

5-(3-Carboxycyclobutyl)-5-(2,4-diethyl-9-thioxanthylmethyl)imidazolidine-2,4-dione (0.4 g, 0.86 mmol) was treated with aqueous sodium hydroxide (1M, 9 ml) and worked up following the procedure described in Example 6 (iv). In addition, the collected solid was stirred as a suspension and filtered sequentially with water, ethanol and ethyl acetate to give the title compound as a grey solid (78 mg, m.p. 203–205° C.) $^1$H NMR (D$_2$0/NaOD) δ 6.98–7.50(m), 2.67(br.d), 1.73–2.28(m), 1.16 (br.d).

EXAMPLE 22

2-Amino-2-(3-cis-carboxycyclobutyl)-3-(1-chloro-4-propoxy-9-thioxanthyl)propionic acid and 2-amino-2-(3-trans-carboxycyclobutyl)-3-(1-chloro-4-propoxy-9-thioxanthyl) propionic acid i) 1-Chloro-9-hydroxy-4-propoxythioxanthene 1-Chloro-4-propoxy-9H-thioxanthen-9-one (20 g, 65.6 mmol) was reduced with sodium borohydride (6.5 g, 0.17 mol) in methanol (320 ml) and worked up following the procedure described in Example 22(i) to give the title compound as a white solid.

ii) Ethyl 2-(1-chloro-4-propoxy-9-thioxanthyl)-3-oxo-3-(3-phenacyloxycarbonylcyclobutyl)propanoate.

1-Chloro-9-hydroxy-4-propoxythioxanthene (0.89 g, 2.89 mmol) was allowed to react with ethyl 3-oxo-3-(3-phenacyloxycarbonylcyclobutyl)propanoate (0.8 g, 2.41 mmol) in ethanol (4 ml) and acetic acid (4 ml) for 4 days and worked up following the procedure described in Example 6(i). The crude product was purified by chromatography on flash silica eluting with diether ether-hexane (3:2) to give the title compound as a pale yellow oil.

iii) 3-[(1-Chloro-4-propoxy-9-thioxanthyl)methylketo] cyclobutanecarboxylic acid.

Ethyl 2-(1-chloro-4-propoxy-9-thioxanthyl)-3-oxo-3-(3-phenacyloxycarbonylcyclobutyl)propanoate (0.75 g, 1.21 mmol) in ethanol (5 ml) was treated with aqueous sodium hydroxide (2M, 3 ml) and the reaction worked up following the procedure described in Example 6 (ii). The crude product was purified by chromatography eluting with diethyl ether-hexane (4:1) to give the title compound as a yellow oil.

iv) 5-(3-Carboxycyclobutyl)-5-(1-chloro-4-propoxy-9-thioxanthylmethyl)imidazolidine-2,4-dione.

A stirred mixture of 3-[1-chloro-4-propoxy-9-thioxanthyl)methylketo]cyclobutane carboxylic acid (0.22 g, 0.51 mmol), potassium cyanide (72 mg, 1.10 mmol) and ammonium carbonate (0.21 g, 2.21 mmol) in ethanol-water (1:1, 4 ml) was heated and then worked up following the procedure described in Example 6(iii) to give the title compound as a foam.

v) 2-Amino-2-(3-cis-carboxycyclobutyl)-3-(1-chloro-4-propoxy-9-thioxanthyl)propionic acid and 2-amino-2-(3-trans-carboxycyclobutyl)-3-(1-chloro-4-propoxy-9-thioxanthyl)propionic acid.

5-(3-carboxycyclobutyl-5-(1-chloro-4-propoxy-9-thioxanthylmethyl)imidazolidine-2,4-dione (0.26 g, 0.51 mmol) was treated with aqueous sodium hydroxide (1M, 5 ml) and worked up following the procedure described in Example 6(iv) to give the title compound as a solid (m.p. 245–247° C. $^1$H2NMR (D$_2$0/NaOD δ 7.44(d), 7.27(t), 7.12 (d), 6.60(d), 3.89(dd), 2.55–2.80(m), 2.13–2.35(m), 1.53–2.10(m), 1.0(d).

EXAMPLE 23

2-Amino-2-(3-cis-carboxymethylcyclobutyl)-3-(9-xanthyl) propanoic acid and 2-amino-2-(3-trans-carboxymethylcyclobutyl)-3-(9-xanthyl)propanoic acid i) Methyl 3-cyanomethylidenylcyclobutane carboxylate To a stirred suspension of sodium hydride (60% dispersion in oil, 6.60 g, 0.17 mol) in dry dimethyl formamide (20 ml) under a nitrogen atmosphere was added a solution of diethyl cyanomethylphosphonate (30.19 g, 0.17 mol) in dry dimethyl formamide (20 ml) dropwise. After 10 minutes at room temperature, a solution of methyl 4-oxocyclobutane carboxylate (20 g, 0.16 mol) in dry dimethyl formamide (20 ml) was added dropwise. After 4 hours, the reaction mixture was diluted with water and extracted four times with diethyl ether. The combined extracts were washed with water, dried, filtered and evaporated to give the title compound as an oil.

ii) Cis- and trans-methyl 3-cyanomethylcyclobutane carboxylate

A solution of methyl 3-cyanomethylidenylcyclobutane carboxylate (23.71 g, 0.16 mol) in a mixture of ethyl acetate (50 ml) and methanol (100 ml) was hydrogenated over 10% palladium-carbon (2.0 g) at 68 psi. After 3 hours, the reaction mixture was filtered through a pad of celite and evaporated to give the title compound as a yellow oil.

iii) 3-Cyanomethylcyclobutanecarboxylic acid

An aqueous solution of sodium hydroxide (1M, 295 ml) was added dropwise over a period of 30 minutes to a stirred solution of methyl 3-cyanomethylcyclobutane carboxylate (21.0 g, 0.20 mol) in methanol (300 ml). After 3 hours, the reaction mixture was washed with hexane (2×75 ml) and the aqueous phase acidified with aqueous hydrochloric acid (2M, 150 ml) to pH5. The aqueous was extracted with ethyl acetate (2×100 ml) and the combined extracts dried, filtered and evaporated to a yellow oil (21 g). The crude product was purified by chromatography on flash silica eluting with diethyl ether to give the title compound as an oil.

iv) 3-Cyanomethylcyclobutanecarbonylchloride

To a stirred solution of 3-cyanomethylcyclobutane carboxylic acid (4.0 g, 28.8 mmol) in dichloromethane (50 ml) was added two drops of dimethylformamide followed by oxalyl chloride (12 ml). The mixture was stirred overnight at room temperature followed by removal of the solvent and excess reagent in vacuo. The resulting oil was dissolved in dry dichloromethane and the solvent evaporated to give the title compound as an oil.

v) Ethyl 3-(3-cyanomethylcyclobutyl)-3-oxopropanoate

A solution of n-butyllithium in hexane (2.5M, 146 ml) was added dropwise to a mechanically stirred solution of ethyl hydrogen malonate (24.3 g, 0.18 ml) in dry tetrahydrofuran (210 ml) cooled to −60° C. under nitrogen atmosphere. After addition, the reaction mixture was stirred at −10° C. for 10 minutes then cooled to −60° C. and a solution of 3-cyanomethylcyclobutanecarbonyl chloride (17.0 g, 0.11 ml) in dry tetrahydrofuran (230 ml) added dropwise at such a rate to maintain temperature below −10° C. The reaction mixture was stirred overnight at room temperature, diluted with aqueous hydrochloric acid (2M, 180 ml) and extracted with diethyl ether (2×200 ml). The combined extracts were washed with a saturated solution of sodium bicarbonate (100 ml), water (100 ml) and brine solution (100 ml), dried, filtered and evaporated to a yellow oil (20.5 g). The crude product was purified by chromatography eluting with diethyl ether-hexane (1:1 and then 3:2) to give the title compound as an oil.

vi) Ethyl 3-(3-cyanomethylcyclobutyl)-3-oxo-2-(9-xanthyl) propanoate

9-Xanthyl (0.52 g, 2.62 mmol) was allowed to react with ethyl 3-(3-cyanomethylcyclobutyl)-3-oxo propanoate (0.50 g, 2.39 mmol) in ethanol (10 ml) and acetic acid (10 ml). Following the procedure described in Example 6(i) to give a yellow oil. The crude product was purified by chromatography on flash silica eluting with hexane-diethyl ether (4:1) to give the title compound as a yellow oil.

vii) 3-(9-Xanthylmethylketo)cyclobutane acetic acid.

Ethyl 3-(3-cyanomethylcyclobutyl)-3-oxo-2-(9-xanthy) propanoate (1.0 g, 2.57 mmol) in ethanol (13 ml) was treated with aqueous sodium hydroxide (2M, 12.8 ml) and the reaction worked up following the procedure described in Example 6(ii). The crude product was purified by chromatograpphy on flash silica eluting with diethyl ether to give the title compound as an oil.

viii) 5-(3-Carboxymethylcyclobutyl)-5-(9-xanthylmethyl) imidazolidine-2,4-dione

A stirred mixture of 3-(9-xanthylmethylketo)cyclobutane acetic acid (0.12 g, 0.36 mmol), potassium cyanide (92 mg, 1.42 mmol) and ammonium carbonate (0.28 g, 2.90 mmol) in ethanol-water (1:1, 3 ml) was heated for 28 hours and then worked up following the procedure described in Example 6(iii). The crude product was recrystallised from acetic acid-water to give the title compound.

ix) 2-Amino-2-(3-cis-carboxymethylcyclobutyl)-3-(9-xanthyl)propanoic acid and 2-amino-2-(3-trans-carboxymethylcyclobutyl)-3-(9-xanthyl)propanoic acid 5-(3-Carboxymethylcyclobutyl)-5-(9-xanthyl methyl) imidazolidine-2,4-dione (24 mg, 0.06 mmol) was treated with aqueous sodium hydroxide (2M, 0.7 ml) and heated at 120° C. for 36 hours. The procedure and work up, following dilution of the reaction mixture with water, is as described in Example 6(iv) to give the title compound as a white solid (m.p. 299–305° C. $^1$H NMR (D$_2$0/NaOD) δ 7.25–7.38(m), 7.11–7.21(m), 4.20(dd), 2.10–2.30(m), 2.01(q), 1.70–1.90 (m), 1.54(dd), 1.28–1.41(m).

EXAMPLE 24

2-Amino-2-(3-cis-carboxymethylcyclobutyl)-3-(9-thioxanthyl)propanoic acid i) Ethyl 3-(3-cyanomethylcyclobutyl)-3-oxo-2-(9-thioxanthyl)propanoate 9-Hydroxythioxanthene (0.4 g, 1.87 mmol) was allowed to react with ethyl 3-(3-cyanomethylcyclobutyl)-3-oxo propanoate (0.36 g, 1.70 mmol) in a mixture of acetic acid (2 ml) and ethanol (2 ml) for 18 hours following the procedure described in Example 6(i). The resulting yellow oil was purified by chromatography on flash silica eluting with diethyl ether-hexane (1:1) to give the title compound as a colourless gum.

ii) 3-(9-Thioxanthylmethylketo)cyclobutaneacetonitrile

A solution of ethyl 3-(3-cyanomethylcyclobutyl)-3-oxo-2-(9-thioxanthyl)propanoate (0.57 g, 1.40 mmol) in a mixture of ethanol (15 ml) and tetrahydrofuran (10 ml) was treated with aqueous sodium hydroxide (2M, 15 ml) and stirred at room temperature for 15 hours. Diluted with water (100 ml), acidified with aqueous hydrochloric acid (2M) and extracted twice with diethyl ether. The combined extracts was dried, filtered and evaporated to an oil (0.42 g). The crude product was purified by chromatography on flash silica eluting with chloroform to give the title compound as an oil.

iii) 5-(3-Cyanomethylcyclobutyl)-5-(9-thioxanthylmethyl)imidazolidine-2,4-dione.

A stirred mixture of 3-(9-thioxanthylmethylketo)cyclobutaneacetonitrile(0.34 g, 1.02 mmol), potassium cyanide (0.13 g, 2.04 mmol) and ammonium carbonate (0.39 g, 4.08 mmol) in ethanol-water (1:1, 4 ml) was heated for 26 hours and then worked up following the procedure described in Example 6(iii) to give the title compound as a white solid.

iv) 2-Amino-2-(3-cis-carboxymethylcyclobutyl)-3-(9-thioxanthyl)propanoic acid 5-(3-Cyanomethylcyclobutyl)-5-(9-thioxanthylmethyl)imidazolidine-2,4-dione(54 mg, 0.13 mmol) in water (0.5 ml) was treated with aqueous sodium hydroxide (2M, 1 ml) and heated at 180° C. for 35 hours and then 200° C. for 5 hours following the procedure described in Example 6(iv). The cooled reaction mixture was diluted with water (2 ml) and washed once with diethyl ether. The aqueous phase was acidified with aqueous hydrochloric acid (5M) and the precipitate filtered to give the title compound as a white solid (m.p.>260° C.) $^1$HNMR (D$_2$0/NaOD) δ 7.25–7.54(m), 4.37 (t), 2.01–2.35(m), 1.75–2.0(m), 1.30–1.19(m).

EXAMPLE 25

Tablets each containing 10 mg of active ingredient are made up as follows:

| Active ingredient | 10 mg |
|---|---|
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 26

Capsules each containing 20 mg of medicament are made as follows:

| Active ingredient | 20 mg |
|---|---|
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

What is claimed is:

1. A compound of the formula:

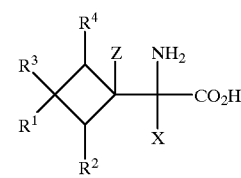

(I)

in which R$^1$ is

Y or Y—C$_{1-6}$ alkyl, where Y is carboxy, tetrazolyl, —SO$_2$H, —SO$_3$H, —OSO$_3$H, —CONHOH, or —P(OH)OR', —PO(OH)OR', —OP(OH)OR' or —OPO(OH)OR' where R' is hydrogen, C$_{1-6}$ alkyl, C$_{2-6}$ alkenyl or optionally substituted phenyl-C$_{1-6}$ alkyl, R$^2$, R$^3$ and R$^4$ are each hydrogen, hydroxyl, halo, carboxy, C$_{1-6}$ alkyl, carboxy-C$_{1-6}$ alkyl, optionally substituted phenyl, optionally substituted phenyl-C$_{1-6}$ alkyl or C$_{2-6}$ alkenyl, X and Z are each hydrogen, C$_{1-6}$ alkyl, C$_{3-7}$ cycloalkyl, optionally substituted phenyl, optionally substituted phenyl-C$_{1-6}$ alkyl, optionally substituted naphthylmethyl, optionally substituted anthracenylmethyl,

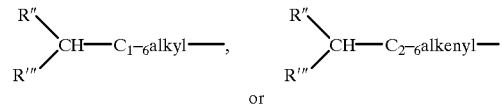

or

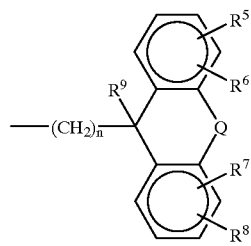

where R" and R'" are optionally substituted phenyl, n is 0 or 1 to 3, Q is —O—, —NH—, —S—, —SO—, —SO$_2$—, —CH$_2$—, —CH=CH—, —CH$_2$S—, —CH$_2$O—, —CH$_2$CH$_2$— or —CONR''''— where R'''' is hydrogen or C$_{1-6}$ alkyl, and R$^5$, R$^6$, R$^7$, R$^8$ and R$^9$ are each hydrogen, halo, C$_{1-6}$ alkyl, C$_{1-6}$ alkyloxy or hydroxy;

provided that one of X and Z is hydrogen, or both of X and Z are hydrogen;

or a salt or ester thereof.

2. A compound according to claim 1 in which R$^1$ is

Y or Y—C$_{1-6}$ alkyl, where Y is carboxy, tetrazolyl, —SO$_2$H, —SO$_3$H, —OSO$_3$H, —CONHOH, or —P(OH)OR', —PO(OH)OR', —OP(OH)OR' or —OPO(OH)OR' where R' is hydrogen, C$_{1-6}$ alkyl, C$_{2-6}$ alkenyl or optionally substituted phenyl-C$_{1-6}$ alkyl, R$^2$, R$^3$ and R$^4$ are each hydrogen, hydroxyl, halo, carboxy, C$_{1-6}$ alkyl, carboxy-C$_{1-6}$ alkyl, optionally substituted phenyl, optionally substituted phenyl-C$_{1-6}$ alkyl or C$_{2-6}$ alkenyl, X and Z are hydrogen, C$_{1-6}$ alkyl, C$_{3-7}$ cycloalkyl, optionally substituted phenyl, optionally substituted phenyl-C$_{1-6}$ alkyl,

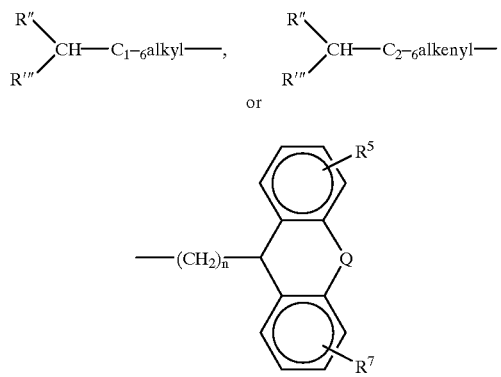

or

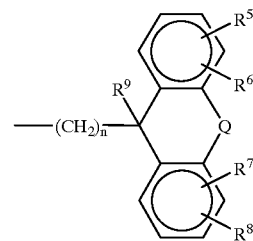

where R'' and R''' are optionally substituted phenyl, n is 0 or 1 to 3, Q is —O—, —NH—, —S—, —CH$_2$—, —CH=CH—, —CONH— or —CH$_2$CH$_2$—, and R$^5$ and R$^7$ are each hydrogen, halo or C$_{1-6}$ alkyl, provided that one of X and Z is hydrogen, or both of X and Z are hydrogen;

or a salt or ester thereof.

3. A compound according to claim 1 in which R$^1$ is

Y or Y—C$_{1-6}$ alkyl-, where Y is carboxy, tetrazolyl, —SO$_2$H, —SO$_3$H, —OSO$_3$H or —CONHOH, R$^2$, R$^3$ and R$^4$ are each hydrogen, hydroxyl, halo, carboxy, C$_{1-6}$ alkyl, carboxy-C$_{1-6}$ alkyl, optionally substituted phenyl, optionally substituted phenyl-C$_{1-6}$ alkyl or C$_{2-6}$ alkenyl, X and Z are each hydrogen, C$_{1-6}$ alkyl, C$_{3-7}$ cycloalkyl, optionally substituted phenyl, optionally substituted phenyl-C$_{1-6}$ alkyl, optionally substituted naphthylmethyl, optionally substituted anthracenylmethyl,

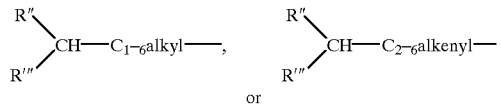

or

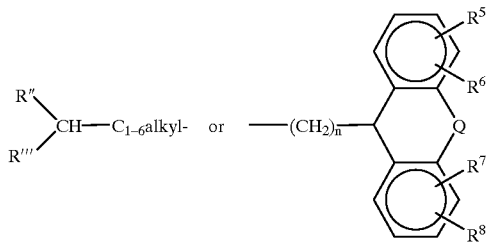

where R'' and R''' are optionally substituted phenyl, n is 0 or 1 to 3, Q is —O—, —NH—, —S—, —SO—, —SO$_2$—, —CH$_2$—, —CH=CH—, —CH$_2$S—, —CH$_2$O—, —CH$_2$CH$_2$— or —CONR''''— where R'''' is hydrogen or C$_{1-6}$ alkyl, and R$^5$, R$^6$, R$^7$, R$^8$ and R$^9$ are each hydrogen, halo, C$_{1-6}$ alkyl, C$_{1-6}$ alkyloxy or hydroxy;

provided that one of X and Z is hydrogen, or both of X and Z are hydrogen;

or a salt or ester thereof.

4. A compound according to claim 3 in which R$^1$ is carboxy or carboxy-C$_{1-6}$ alkyl.

5. A compound according to claim 3 or claim 4 in which X is n is 1 and Q is —O— or —S—.

6. A compound according to claim 5 in which R$^2$ and R$^4$ are hydrogen, carboxy or optionally substituted phenyl, and R$^3$ is hydrogen or carboxy.

7. A compound according to claim 1 in which R$^1$ is carboxy, R$^2$, R$^3$ and R$^4$ are hydrogen, X is R'' R''' CH—C$_{1-6}$ alkyl or

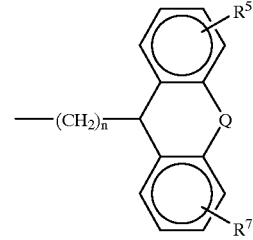

where n is 1 and Q is —O— or —S—.

8. A pharmaceutical formulation comprising a pharmaceutically effective amount of a compound of formula I according to claim 1 or a pharmaceutically acceptable salt or ester thereof, together with a pharmaceutically acceptable diluent or carrier therefor.

9. A method of treating an animal suffering from or susceptible to a disorder of the central nervous system, which comprises administering a pharmaceutically effective amount of a compound of formula I according to claim 1, or a pharmaceutically acceptable salt or ester thereof.

10. A method as claimed in claim 9, in which said animal is a human.

* * * * *